United States Patent [19]
Findeisen et al.

[11] 4,146,723
[45] Mar. 27, 1979

[54] HETEROCYCLIC DIISOCYANATES AND A PROCESS FOR MAKING POLYURETHANES AND POLYURETHANE-UREAS

[75] Inventors: Kurt Findeisen, Leverkusen; Kuno Wagner, Leverkusen-Steinbuechel; Erich Klauke, Odenthal-Hahnenberg, all of Fed. Rep. of Germany

[73] Assignee: Bayer Aktiengesellschaft, Leverkusen, Fed. Rep. of Germany

[21] Appl. No.: 457,290

[22] Filed: Apr. 2, 1974

[30] Foreign Application Priority Data

Apr. 11, 1973 [DE] Fed. Rep. of Germany ....... 2318170

[51] Int. Cl.$^2$ ................. C07D 251/00; C07D 275/00; C07D 233/40
[52] U.S. Cl. ............................. 548/307; 260/302 D; 528/73; 528/67; 544/222; 548/314
[58] Field of Search ............... 260/309.7, 302 D; 544/222; 548/307, 314

[56] References Cited

U.S. PATENT DOCUMENTS

| | | | |
|---|---|---|---|
| 2,514,353 | 7/1950 | Walter | 260/309.7 |
| 2,526,757 | 10/1950 | Larson et al. | 260/309.7 |
| 3,410,866 | 11/1968 | Middleton | 260/309.6 |
| 3,787,435 | 1/1974 | Scholl et al. | 260/309.7 X |
| 3,912,754 | 10/1975 | Findeisen et al. | 548/307 |

FOREIGN PATENT DOCUMENTS

| | | | |
|---|---|---|---|
| 1302248 | 1/1973 | United Kingdom | 260/309.5 |
| 1303323 | 1/1973 | United Kingdom | 260/309.5 |

OTHER PUBLICATIONS

Chem. Abstracts 82:125981 v.

*Primary Examiner*—Ethel G. Love
*Attorney, Agent, or Firm*—Gene Harsh; Joseph C. Gil

[57] ABSTRACT

Novel heterocyclic diisocyanates are prepared by reacting a urea diisocyanate of the formula

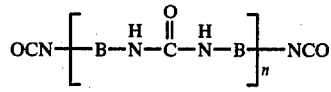

in which B is a divalent organic radical and n is an integer of 1 to 3 with a compound having the formula

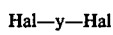

in which y is —C—C—; —C—S—; —C—N—C—; —S—N—C. The novel heterocyclic diisocyanates are useful in making polyurethanes and polyurethane-ureas having improved chemical and temperature resistance.

5 Claims, No Drawings

HETEROCYCLIC DIISOCYANATES AND A PROCESS FOR MAKING POLYURETHANES AND POLYURETHANE-UREAS

This invention relates generally to organic diisocyanates and more particularly to heterocyclic diisocyanates and to a process for producing them.

Organic polyisocyanates are reacted with organic compounds having reactive hydrogen atoms determinable by the Zerewitinoff method to make non-porous and cellular polyurethanes. The heretofore available polyisocyanates can be used advantageously in the manufacture of most polyurethanes but are not entirely suitable in some instances for making high temperature and chemical resistant foils and lacquers.

It is therefore an object of this invention to provide novel organic diisocyanates which can be used to advantage in reactions with organic compounds having reactive hydrogen containing groups. Another object of the invention is to provide novel heterocyclic diisocyanates which can be substituted for or used along with the heretofore available polyisocyanates in the manufacture of polyurethane resins. A more specific object of the invention is to provide novel heterocyclic diisocyanates which can be used to advantage in making chemical and heat resistant lacquers and films.

The foregoing objects and others are accomplished in accordance with this invention, generally speaking by providing heterocyclic diisocyanates of the general formula

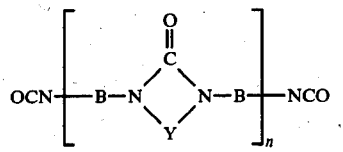

in which B represents a divalent organic radical, y represents a divalent radical containing one of the following sequences of atoms —C—C—; —C—S—; —C—N—C; or —S—N—C in the linear chain and n represents an integer of from 1 to 3. B may in particular represent divalent aliphatic, cycloaliphatic, araliphatic or aromatic radicals or multi-nuclear aromatic radicals bridged by methylene, oxygen or sulphur groups; these radicals may be substituted one or more times with alkyl groups or alkoxy groups having one to six carbon atoms or with chlorine. The following are examples of radicals represented by B: alkylene radicals containing 5 or 6 carbon atoms such as $C_5H_{10}$— and $C_6H_{12}$—, cycloalkylene radicals containing 5 or 6 carbon atoms such as $C_5H_8$— and $C_6H_{10}$—, phenylene radicals, diphenylmethane radicals, diphenylether and diphenylthioether radicals which may be substituted one or more times with alkyl groups or alkoxy groups containing one to six carbon atoms such as methyl, ethyl, propyl, butyl, amyl, hexyl, methoxy, ethoxy, propoxy, butoxy, amoxy, hexoxy or chlorine.

The radicals represented by y may be the radicals having the chains indicated above in which the free valencies of the carbon atoms are substituted with hydrogen, oxygen or nitrogen, the free valencies of the nitrogen atoms are subtituted with hydrogen or alkyl having one to six carbon atoms and the free valencies of the sulphur atoms are substituted with oxygen. The following are examples of radicals y:

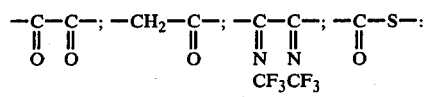

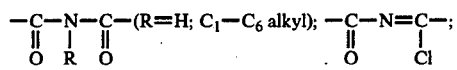

The invention also provides a process for making heterocyclic diisocyanates of formula I above which is characterised in that a urea derivative of the formula

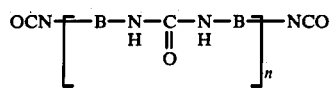

in which B and n have the meanings indicated above are reacted with compounds of the formula

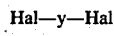

in which y has the meanings indicated above and Hal represents halogen (preferably chlorine or fluorine), at temperatures of about 0° to about 200° C. and optionally in an inert organic diluent, the reaction being accompanied by ring closure.

The reaction is preferably carried out in the presence of a liquid organic diluent such as for example polar inert solvents having a boiling point of from about 30° to about 200° C. such as methylene chloride, o-dichlorobenzene, acetonitrile, chlorobenzene and the like as a reaction medium. The urea diisocyanate of formula II need not be soluble in the diluent because the reaction may also be carried out in a heterogeneous phase. The heterocyclic diisocyanates provided by the invention are generally soluble in the solvents used so that termination of the reaction can be recognized by the formation of a clear solution and cessation of evolution of gas.

The reaction is carried out within the temperature range of about 0° to about 200° C., preferably at about 20° to about 140° C. and more particularly at about 20° to about 60° C.

Any suitable diluent which is non-reactive with the urea diisocyanate, the compound Hal—y—Hal or the resulting diisocyanate may be used such as for example, halogenated aliphatic hydrocarbons such as methylene chloride, chloroform, dichloroethylene and trichloroethylene, halogenated aromatic compounds such as chlorobenzene, dichlorobenzene and trichlorobenzene as well as dioxane, ethyl acetate, acetone, acetonitrile, toluene, xylene and the like may be used.

The reaction provided by the invention may be catalyzed with bases although it is generally not necessary to use a catalyst. In exceptional cases, tertiary bases are added to obtain a more rapid reaction. Particularly suitable catalysts are triethylamine, diazabicyclo-(2,2,2)-octane, 1,5-diazabicyclo(4,3,0)-non-5-ene, I,8-diazabicyclo-(5,4,0)-undec-7-ene, dimethyl aniline, dimethyl benzylamine and pyridine.

Any urea diisocyanate of formula II may be used as the starting material. Such ureas can be prepared easily by the process described in French Patent Specification No. 1,103,329.

The following are examples of particularly suitable urea diisocyanates:

N,N'-di-(ω-isocyanato)-hexamethylene-urea;
N,N'-di-(3-isocyanato-4-chloro)-phenyl-urea;
N,N'-di-(3-isocyanato-4-methyl)-phenyl-urea;
N,N'-di-(3-isocyanato-4-methoxy)-phenyl-urea;
N,N'-di-(methyl-3-isocyanato-5-dimethyl-cyclohexyl)methylene-urea;
N,N'-di-[m-(γ-isocyanato)-butyl]-phenyl-urea;
4-bis-N,N'-(4'-isocyanato)-diphenylmethane-urea;
4-bis-N,N'-(4'-isocyanato)-diphenylether-urea;
4-bis-N,N'-(4'-isocyanato)-diphenylthioether-urea.

The α, β- and α, γ-bifunctional compounds of the formula Hal-y-Hal used for ring closure are also already known (see e.g. DOS No. 1,768,179; DBP No. 1,224,720; synthesis, 1970, 542; DOS No. 1,932,830; DOS No. 2,013,433).

The term "α, β- and α, γ-bifunctional compounds" (which corresponds to 1,2- and 1,3-bifunctional compounds) is therefore used in the context of this invention to denote substances which react under the given reaction conditions to split off at least one mol of hydrogen chloride.

The following are mentioned as examples of α, β-bifunctional compounds: oxalyl chloride, chloroacetyl chloride, perfluorodiaza-2,5-hexadiene-(2,4) and chlorocarbonyl-sulphenic acid chloride. The following are examples of α, γ-bifunctional compounds: chlorocarbonyl isocyanate, bis-(chlorocarbonyl)-amines, chlorocarbonyl isocyanide dichloride and chlorosulphonyl isocyanate.

The reaction of ureas free from isocyanato groups with "α, β- and α, γ-bifunctional compounds" is already known in principle (see Berichte 46, 1399; Angew. Chem. 82, 67 (1970) and DOS No. 1,927,921).

In all these reactions, ring closure takes place only if the urea is free from substituents which would react with the so-called α, β- or α, γ-bifunctional compounds.

The isocyanate group is a particularly reactive substituent. It is therefore completely unexpected to find that urea diisocyanates can react with α, β- and α, γ-bifunctional compounds to be converted into heterocyclic diisocyanates while yet preserving the isocyanato groups and without side reactions taking place to any substantial extent. It is all the more surprising since it has been disclosed in DOS No. 1,518,873 that oxalyl chloride reacts with isocyanates to form N-halogen-carbonyl-N-halogenoxyalkyl-amines.

Usually two mols (but at least one mol) of hydrogen halide are generally split off in the reactions according to the invention. Now it is known that hydrogen halides will undergo addition reactions with isocyanates even at room temperature to form carbamic acid chlorides (Houben-Weyl, Methoden der Organischen Chemie Volume VIII, Sauerstoffverbindungen III pages 130 to 131). It is surprising to find that such a reaction does not take place in this case. The "α, β- and α, γ-bifunctional compounds" used according to the invention all contain a carboxylic acid chloride group or a similarly reactive group. It is well known that carboxylic acid chlorides react with isocyanates to form N-substituted N-acrylcarbamic acid halides. This reaction also fails to take place in the process according to the invention.

The following are specific examples of new heterocyclic diisocyanates which can be prepared in accordance with the invention:

N,N'-di(3-isocyanato-4-methyl)-phenyl-parabanic acid;
" -phenyl-hydantoin;
" -phenyl-1,2,4-thiadiazolidine-3,5-dione;
" -phenyl-2,3-bis-trifluoro-methyl-iminoimidazolone-(5);
" -phenyl-isocyanuric acid;
" -phenyl-N"-methyl-isocyanuric acid;
" -phenyl-N"-phenyl-isocyanuric acid;
" -phenyl-N"-p-chlorophenyl-isocyanuric acid;
" -phenyl-N"-3,4-dichloro-phenyl-isocyanuric acid;

N,N'-di-(ω-isocyanato)-hexmethylene-parabanic acid;
" -hydantoin;
" -1,2,4-thiadiazolidine-3,5-dione;
" -2,3-bis-trifluoromethyl-iminoimidazolone-(5);
" -isocyanuric acid;
" -N"-methyl-isocyanuric acid;
" -N"-phenyl-isocyanuric acid;
" -N-41 -p-chlorophenyl-isocyanuric acid;
" -N"-3,4-dichlorophenyl-isocyanuric acid;

N,N'-di-(3-isocyanato-4-chloro)-phenyl-parabanic acid;
" -hydantoin;
" -1,2,4-thiadiazolidine-3,5-dione;
" -2,3-bis-trifluoromethyl-iminoimidazolone-(5);
" -isocyanuric acid;
" -N"-methyl-isocyanuric acid;
" -N"-phenyl-isocyanuric acid;
" -N"-p-chlorophenyl-isocyanuric acid;
" -N"-3,4-dichlorophenyl-isocyanuric acid;

N,N'-di-(3-isocyanato-4-methoxy)-phenyl-parabanic acid;
" -hydantoin;
" -1,2,4-thiadiazolidine-3,5-dione;
" -2,3-bis-trifluoromethyl-iminoimidazolone-(5);
" -isocyanuric acid;
" -N"-methyl-isocyanuric acid;

N,N'-di-(3-isocyanato-4-methoxy)-phenyl-N"-phenyl-isocyanuric acid;
" -N"-p-chlorophenyl-isocyanuric acid;
" -N"-3,4-dichlorophenyl-isocyanuric acid;

N,N'-di-(methyl-3-isocyanato-5-dimethyl-cyclohexyl)-mehtylene-parabanic acid;
" -hydantoin;
" -1,2,4-thiadiazolidine-3,5-dione;
" -2,3-bis-trifluoromethyl-iminoimidazolone-(5);
" -isocyanuric acid;
" -N"-methyl-isocyanuric acid;
" -N"-phenyl-isocyanuric acid;
" -N"-p-chlorophenyl-isocyanuric acid;
" -N"-3,4-dichlorophenyl-isocyanuric acid;

N,N'-di-[m-(γ-isocyanato)-butyl]-phenyl-parabanic acid;
" -hydantoin;
" -1,2,4-thiadiazolidine-3,5-dione;
" -2,3-bis-trifluoromethyl-iminoimidazolone-(5);
" -isocyanuric acid;
" -N"-methyl-isocyanuric acid;
" -N"-phenyl-isocyanuric acid;
" -N"-p-chlorophenyl-isocyanuric acid;
" -N"-3,4-dichlorophenyl-isocyanuric acid;

4-bis-N,N'-(4'-isocyanato)-diphenylmethane-parabanic acid;
" -hydantoin;
" -1,2,4-thiadiazolidine-3,5-dione;
" -2,3-bis-trifluoro-methyl-iminoimidazolone-(5);
" -isocyanuric acid;
" -N"-methyl-isocyanuric acid;
" -N"-phenyl-isocyanuric acid;
" -N"-p-chlorophenyl-isocyanuric acid;
" -N"-3,4-dichlorophenyl-isocyanuric acid;

4-bis-N,N'-(4'-isocyanato)-diphenylether-parabanic acid;
" -hydantoin;
" -1,2,4-thiadiazolidine-3,5-dione;
" -2,3-bis-trifluoromethyl-iminoimidazolone-(5);

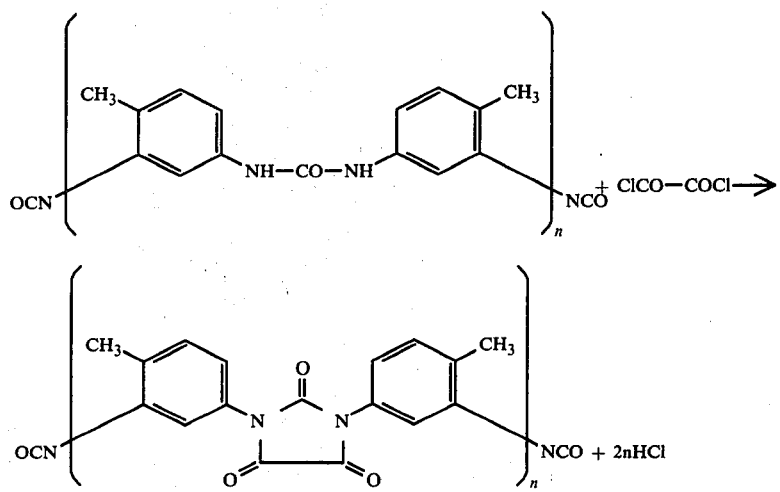

|   |   |
|---|---|
| " | -isocyanuric acid; |
| " | -N"-methyl-isocyanuric acid; |
| " | -N"-phenyl-isocyanuric acid; |
| " | -N"-p-chlorophenyl-isocyanuric acid; |
| " | -N"-3,4-dichlorophenyl-isocyanuric acid; |
| 4-bis-N,N'-(4'-isocyanato)-diphenylthioether-parabanic acid; |   |
| " | -hydantoin; |
| " | -1,2,4-thiadiazolidine-3,5-dione; |
| " | -2,3-bis-trifluoromethyl-iminoimidazolone-(5); |
| " | -isocyanuric acid; |
| " | -N"-methyl-isocyanuric acid; |
| " | -N"-phenyl-isocyanuric acid; |
| " | -N"-p-chlorophenyl-isocyanuric acid; |
| " | -N"-3,4-dichloro-phenyl-isocyanuric acid. |

Preparation of the new heterocyclic diisocyanates will now be explained in more detail with the aid of two examples: 1. A urea diisocyanate of formula II is suspended in methylene chloride, and one mol of oxalyl chloride is then added. Hydrogen chloride starts to evolve within a short time and urea diisocyanate slowly dissolves. When all of the urea diisocyanate has completely dissolved, the reaction mixture is heated to 45° C. (reflux) for some time to complete the reaction. This reaction is illustrated by the following equation:

n is an integer of 1 to 3.

The slightly cloudy solution is filtered and methylene chloride is distilled off. The residue is recrystallized from xylene. Oxalyl chloride is a "α, β-bifunctional compound" within the meaning of this invention. A 5-membered heterocyclic ring is therefore formed. 2. A urea diisocyanate of formula II is suspended in methylene chloride, and chlorocarbonyl isocyanate is added dropwise.

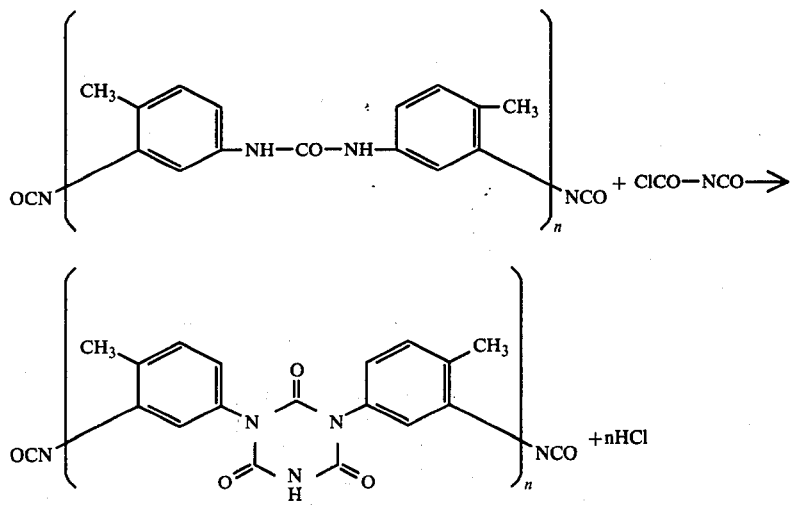

n is an integer of 1 to 3.

The methylene chloride is slowly heated to boiling and kept at this temperature until evolution of hydrogen chloride ceases. The urea diisocyanate is then found to have dissolved. After removal of methylene chloride by evarporation, the desired diisocyanate remains behind in the form of a white powder. A "α, γ-bifunctional compound" was used in this case and therefore a 6-membered heterocyclic ring was formed.

The new heterocyclic diisocyanates provided by the invention are suitable for all the known applications of diisocyanates, for example low-molecular weight derivatives (urethanes, ureas, phosphorus derivatives, sulphur compounds etc.) may be used as pesticide for plant protection. In addition, products which are suitable for use as coatings, as polyurethane elastomers and for producing molded products, including molded polyurethane foam products, may be produced by the known methods of polyisocyanate polyaddition with one of the new diisocyanates.

The new heterocyclic diisocyanates are particularly important for producing temperature-resistant lacquers and foils.

High-molecular weight substances which are resistant to acid chemicals can be produced by controlled incorporation of the new heterocyclic diisocyanates and in particular of parabanic acid diisocyanate.

For the synthesis of polymers, the new heterocyclic diisocyanates may also be used as mixtures, e.g. together with known polyisocyanates. Polymers which contain parabanic acid residues and hydantoin residues are improved in their stabilitty to acids and have excellent resistance to high temperatures.

EXAMPLE 1

32.2 g (0.1 mol) of N,N'-di-(3-isocyanato-4-methyl)-phenyl-urea are suspended in 250 ml of anhydrous acetonitrile in a three-necked flask and heated. 34.2 g (0.15 mol) of perfluorodiaza-2,5-hexadiene-(2,4) are added dropwise in the course of 3 hours at the boiling point of acetonitrile. The reaction is completed by heating to 80° C. A clear solution is obtained after 4 hours. The acetonitrile is evaporated off in a rotary evaporator. The dry residue is a diisocyanate of the formula

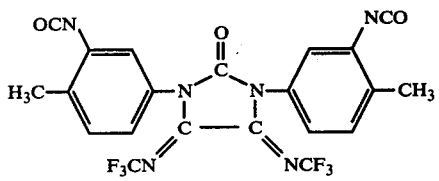

Yield: 32.6 g=64% of the theory;
Molecular weight determination by mass spectroscopy:
510, calculated; 510;
% NCO theoretical: 16.48,
% NCO found: 16.20.

EXAMPLE 2

64.4 g of N,N'-di-(3-isocyanato-4-methyl)-phenyl-urea 0.2 mol) are suspended in 500 ml of methylene chloride, and 25.4 g of oxalyl chloride (0.2 mol) are added dropwise at room temperature in the course of one hour. As stirring is continued, the temperature rises to 40° C. and hydrogen chloride begins to evolve. After a further 3 hours boiling under reflux, evolution of gas has ceased and a clear solution has been obtained. After removal of the methylene chloride by evaporation in a rotary evaporator, the residue obtained is recrystallized from xylene.

Yield: 70 g=93% of the theory of N,N'-di-(3-isocyanato-4-methyl)-phenyl-parabanic acid.
Melting point: 235°–238° C.

| Analysis: | C | H | N | O |
|---|---|---|---|---|
| Calculated: | 60.64 | 3.21 | 14.89 | 21.26 |
| Found: | 60.6 | 3.5 | 14.7 | 21.1 |

EXAMPLE 3

64.4 g of N,N'-di-(3-isocyanato-4-methyl)-phenyl-urea (0.2 mol) are suspended in 300 ml of o-dichlorobenzene in a three-necked flask, and 22.6 g of chloroacetyl chloride (0.2 mol) are added dropwise at room temperature. The reaction mixture is heated until evolution of gas sets in at 120° C. The reaction product goes into solution when evolution of hydrogen chloride again starts to evolve. When the dark colored solution obtained has cooled down, it is clarified with active charcoal and the o-dichlorobenzene is distilled off under reduced pressure. The residue is triturated with petroleum ether and the precipitated reaction product is suction-filtered and dried.

Yield: 45 g=62% of the theory of N,N'-di-(3-isocyanato-4-methyl)-phenyl-hydantoin

| Analysis: | C | H | N | O |
|---|---|---|---|---|
| Calculated: | 62.98 | 3.89 | 15.46 | 17.66 |
| Found: | 63.0 | 4.12 | 15.2 | 17.5 |

EXAMPLE 4

64.4 g of N,N'-di-(3-isocyanato-4-methyl)-phenyl-urea (0.2 mol) are introduced into 400 ml of chlorobenzene. 26.2 g of chlorocarbonyl sulphenyl chloride (0.2 mol) are added dropwise in the course of 10 minutes. The reaction mixture is heated to 125° C. and kept at this temperature for 5 hours. After cooling to room temperature, the reaction mixture is filtered, the solvent is evaporated off in a rotary evaporator and the reaction product is precipitated with cleaning petrol.

Yield: 42 g=55% of the theory of N,N'-di-(3-isocyanato-4-methyl)-phenyl-1,2,4-thiadiazolidine-3,5-dione

| Analysis: | C | H | N | O | S |
|---|---|---|---|---|---|
| Calculated: | 56.84 | 3.18 | 14.73 | 16.83 | 8.41 |
| Found: | 56.9 | 3.30 | 14.5 | 16.7 | 8.35 |

EXAMPLE 5

64.4 g of N,N'-di-(3-isocyanato-4-methyl)-phenyl-urea (0.2 mol) are introduced into 400 ml of methylene chloride. 32 g of chlorocarbonyl isocyanate (0.3 mol) are then added dropwise at room temperature with stirring in the course of 30 minutes. The reaction mixture is heated to 40° C. until evolution of hydrogen chloride has terminated. The resulting almost clear methylene chloride solution is filtered hot. The methylene chloride is then distilled off and replaced by 200 ml of chlorobenzene. The solution is then briefly heated to 130° C. When the reaction mixture is cold, it is evaporated to dryness in a rotary evaporator.

The reaction product may be purified by boiling with toluene, filtering and precipitating with cleaning petrol.
Yield: 72.5 g=93% of the theory of N,N'-di-(3-isocyanato-4-methyl)-phenyl-isocyanuric acid.
% NCO theoretical: 21.4
% NCO found: 21.6

| Analysis: | C | H | N | O |
|---|---|---|---|---|
| Calculated: | 58.31 | 3.35 | 17.9 | 20.44 |
| Found: | 58.2 | 3.11 | 18.2 | 20.7 |

EXAMPLE 6

32.2 g of N,N'-di-(3-isocyanato-4-methyl)-phenyl-urea (0.1 mol) are suspended in 200 ml of chlorobenzene. A solution of 15.6 g of N-methyl-bis-chlorocarbonyl-amine (0.1 mol) in 30 ml of chlorobenzene is added dropwise at room temperature. The reaction mixture is heated to 50° C., slight evolution of hydrogen chloride being observed. The reaction mixture is left to cool and 20.2 g of triethylamine (0.2 mol) are then added dropwise at room temperature. The reaction mixture is again heated to 50° C. and kept at this temperature for 2 hours. When the reaction mixture is cold, the solvent is distilled off and the residue is taken up with xylene which causes the triethylamine hydrochloride to precipitate while the desired reaction product remains in solution. After removal of the solvent by distillation, the desired reaction produce is left behind.

Yield: 25 g=61.5% of the theory of N,N'-di-(3-isocyanato-4-methyl)-phenyl-N"-methylisocyanuric acid

| Analysis: | C | H | N | O |
|---|---|---|---|---|
| Calculated: | 59.26 | 3.73 | 17.28 | 19.74 |
| Found: | 59.5 | 3.8 | 17.0 | 19.6 |

EXAMPLE 7

100 parts by weight of a polyester of phthalic acid anhydride and trimethylolpropane with OH-content 8.5% in the form of a 20% solution in ethyl glycol acetate are mixed with 94 parts by weight of N,N'-di-(3-isocyanato-4-methyl-phenylparabanic acid. The reaction mixture is cast on a glass support. After evaporation of the solvent, cross-linked, glossy, solvent-resistant films are obtained.

Any of the other urea diisocyanates and compounds of the formula

Hal—y—Hal indicated as suitable herein can be substituted for those of the foregoing working examples to produce corresponding heterocyclic diisocyanates.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate having the formula

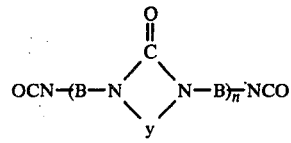

in which

B represents a phenylene radical or a ddiphenyll methane radical each of which may be substituted one or more times with alkyl groups;

y represents a divalent radical containing a sequence of —C—C— atoms in the linear chain, and n is an integer from 1 to 3.

2. A compound of the formula

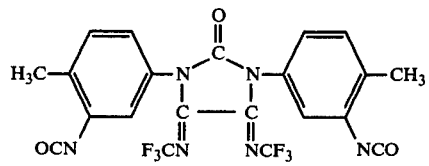

3. A process for preparing diisocyanates which comprises reacting (1) a urea diisocyanate of the formula

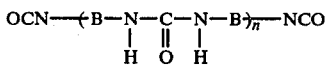

in which B represents a divalent aliphatic radical, a cycloaliphatic radical, an araliphatic radical, an aromatic radical, a multi-nuclear aromatic radical bridged by methylene, oxygen or sulphur groups and any one of said radicals substituted one or more times with an alkyl group or an alkoxy group having one to six carbon atoms or with chlorine, and n is an integer of from 1 to 3 with (2) a compound of the formula: Hal—y—Hal, in which y represents a divalent radical containing one of the following sequence of atoms —C—C; —C—S—; —C—N—C—; or —S—N—C— in the linear chain, and Hal represents a halogen atom, said reaction being conducted at a temperature from 0° to 200° C. and said reaction being accompanied by ring closure.

4. The process of claim 3 wherein the reaction is conducted in a liquid organic diluent which is non-reactive with the reactants and product.

5. The process of claim 3 wherein y represents a divalent radical containing a —C—C— sequence of atoms in the linear chain.

* * * * *